United States Patent [19]
Matsuura et al.

[11] Patent Number: 5,525,476
[45] Date of Patent: Jun. 11, 1996

[54] IMMUNOASSAY, MONOCLONAL ANTIBODY, AND HYBRIDOMA

[75] Inventors: Shiro Matsuura, Tokyo; Yutaka Takagaki, Nara; Yonekazu Hamano, Osaka; Ken Fukushi, Tokyo; Keigo Kabasawa, Tokyo; Hiroshi Kita, Tokyo, all of Japan

[73] Assignees: Iatron Laboratories, Inc., Tokyo; Osakafu, Osaka, both of Japan

[21] Appl. No.: 39,085

[22] PCT Filed: Aug. 10, 1992

[86] PCT No.: PCT/JP92/01021

§ 371 Date: Apr. 27, 1993

§ 102(e) Date: Apr. 27, 1993

[87] PCT Pub. No.: WO93/03365

PCT Pub. Date: Feb. 18, 1993

[30] Foreign Application Priority Data

Aug. 9, 1991 [JP] Japan ................. 3-224864
Oct. 26, 1991 [JP] Japan ................. 3-306859

[51] Int. Cl.$^6$ ............................................. G01N 33/577
[52] U.S. Cl. .................. 435/7.94; 435/7.93; 436/548; 436/815
[58] Field of Search ............... 435/240.27, 7.93, 435/7.94; 436/548, 815

[56] References Cited

U.S. PATENT DOCUMENTS

| | | | |
|---|---|---|---|
| 5,171,664 | 12/1992 | Uda et al. | 435/7.1 |
| 5,180,665 | 1/1993 | Holmes | 436/503 |
| 5,206,141 | 4/1993 | Park | 436/531 |

FOREIGN PATENT DOCUMENTS 1-156666  6/1989  Japan.

OTHER PUBLICATIONS

S. Matsuura et al., J. Biochem. (Tokyo), 114(2), 273–278 (1993).

L. Uda et al., Chem. Abstracts, vol. 112, No. 2150d (1989).

Y. Hokama et al., Chem. Abstracts, vol. 112, No. 214837h (1989).

A. Kogawa et al., Chem. Abstracts, vol. 113, No. 2794m (1989).

Y. Hamano et al., Chem. Abstracts vol. 115, No. 107923y (1991).

L. Usagawa et al., Chem. Abstracts, vol. 112, No. 113673w (1989).

*Primary Examiner*—Mary E. Ceperley
*Attorney, Agent, or Firm*—Sherman and Shalloway

[57] ABSTRACT

The present invention relates to a method for determining a lipophilic compound, comprising using an antibody tolerant to one or more organic solvents, and carrying out an antigen-antibody reaction in the presence of one or more organic solvents. By the present method, it is possible to perform an antigen-antibody reaction of the lipophilic compound and the antibody, using an extract of a sample by one or more organic solvents, and thus the procedure becomes simple.

Further, the present invention also relates to a monoclonal antibody specific to at least okadaic acid, dinophysistoxin-1 and dinophysistoxin-3, a hybridoma which produces the above monoclonal antibody, and an immunological determination method of diarrheal shellfish poisons using the above monoclonal antibody. According to the present invention, specific determination of all the three types of diarrheal shellfish poisons becomes possible.

6 Claims, 14 Drawing Sheets a Water (0% Methyl Alcohol Aqueous Solution)
b 10% Methyl Alcohol Aqueous Solution
c 20% Methyl Alcohol Aqueous Solution
d 30% Methyl Alcohol Aqueous Solution
e 40% Methyl Alcohol Aqueous Solution f  50% Methyl Alcohol Aqueous Solution
g  60% Methyl Alcohol Aqueous Solution
h  70% Methyl Alcohol Aqueous Solution
i  80% Methyl Alcohol Aqueous Solution
j  90% Methyl Alcohol Aqueous Solution
k  100% Methyl Alcohol a Water (0% Methyl Alcohol Aqueous Solution)
b 10% Methyl Alcohol Aqueous Solution
c 20% Methyl Alcohol Aqueous Solution
d 30% Methyl Alcohol Aqueous Solution
e 40% Methyl Alcohol Aqueous Solution f  50% Methyl Alcohol Aqueous Solution
g  60% Methyl Alcohol Aqueous Solution
h  70% Methyl Alcohol Aqueous Solution
i  80% Methyl Alcohol Aqueous Solution
j  90% Methyl Alcohol Aqueous Solution
k  100% Methyl Alcohol a Water (0% Methyl Alcohol Aqueous Solution)
b 10% Methyl Alcohol Aqueous Solution
c 20% Methyl Alcohol Aqueous Solution
d 30% Methyl Alcohol Aqueous Solution
e 40% Methyl Alcohol Aqueous Solution f  50% Methyl Alcohol Aqueous Solution
g  60% Methyl Alcohol Aqueous Solution
h  70% Methyl Alcohol Aqueous Solution
i  80% Methyl Alcohol Aqueous Solution
j  90% Methyl Alcohol Aqueous Solution
k  100% Methyl Alcohol a Water (0% Methyl Alcohol Aqueous Solution)
b 10% Methyl Alcohol Aqueous Solution
c 20% Methyl Alcohol Aqueous Solution
d 30% Methyl Alcohol Aqueous Solution
e 40% Methyl Alcohol Aqueous Solution
f 50% Methyl Alcohol Aqueous Solution
g 60% Methyl Alcohol Aqueous Solution
h 70% Methyl Alcohol Aqueous Solution a Water (0% Methyl Alcohol Aqueous Solution)
b 10% Methyl Alcohol Aqueous Solution
c 20% Methyl Alcohol Aqueous Solution
d 30% Methyl Alcohol Aqueous Solution
e 40% Methyl Alcohol Aqueous Solution
f 50% Methyl Alcohol Aqueous Solution
g 60% Methyl Alcohol Aqueous Solution
h 70% Methyl Alcohol Aqueous Solutio a  Water (0% Methyl Alcohol Aqueous Solution)
b  10% Methyl Alcohol Aqueous Solution
c  20% Methyl Alcohol Aqueous Solution
d  30% Methyl Alcohol Aqueous Solution
e  40% Methyl Alcohol Aqueous Solution
f  50% Methyl Alcohol Aqueous Solution
g  60% Methyl Alcohol Aqueous Solution
h  70% Methyl Alcohol Aqueous Solution

IMMUNOASSAY, MONOCLONAL ANTIBODY, AND HYBRIDOMA

TECHNICAL FIELD

The present invention relates to a method for the determination of a lipophilic (oil-soluble) compound, more particularly relates to a method for the inmunological determination of a lipophilic compound by extracting the lipophilic compound from a sample by an organic solvent, and effecting an antigen-antibody reaction in the presence of an organic solvent, using an organic solvent-resistant antibody against the lipophilic compound.

Furthermore, the present invention relates to a monoclonal antibody specific to diarrheal shellfish poisons, a hybridoma producing the monoclonal antibody, and a method for determining diarrheal shellfish poisons using the monoclonal antibody. The monoclonal antibody according to the present invention is in particular an antibody resistant to an organic solvent.

BACKGROUND ART

In various noxious compounds such as pesticides or toxins, and biologically active important substances such as hormones, there are many compounds which are sparingly soluble in water, but soluble in oil. Hitherto, when the qualitative and quantitative determination of a hydrophobic (water-sparingly-soluble) but lipophilic compound is carried out, the hydrophobic but lipophilic compound to be examined was extracted from a sample by an appropriate organic solvent and purified, and then various instrumental analyses or the like were performed. These procedures were cumbersome and time-consuming in comparison with the case of hydrophilic (water-soluble) compounds which can be directly qualitatively and quantitatively assayed. For example, when assaying okadaic acid which is a toxin contained in marine products, in particular, a diarrheal shellfish poison contained in bivalves such as scallops, the extraction was performed by acetone, ether, ethyl alcohol or methyl alcohol, and the extract was concentrated if necessary, and the assay was carried out by high performance liquid chromatography.

Further, when assaying the above hydrophobic but lipophilic compounds by the immunological method, it was necessary, prior to the determination, to extract the sample possibly containing the substance to be examined by an organic solvent selected in accordance with the extent of the oil solubility of the substance in question. These procedures were cumbersome and time-consuming in comparison with the case of hydrophilic compounds. Further, if there remained the organic solvent used for the extraction, the immunoreaction would be inhibited and thus the reaction would not proceed, or extremely inaccurate results would be obtained in the assay, depending on the concentration of the remaining solvent. To remedy such an inaccurate immunoassay, the organic solvent extract of the lipophilic compound might be diluted with water to lower the concentration of the organic solvent to a concentration where the immunoreaction proceeds accurately (for example, 40% or less). However, even if the immunoreaction could proceed accurately, the solubility of the lipophilic compound per se would be reduced and thus an accurate assay still could not be performed.

Therefore, one of the objects of the present invention is to provide a means enabling swift and specific assay of a hydrophobic but lipophilic compound by immunological means using an antibody.

In the meanwhile, there exist three kinds of diarrheal shellfish poisons; okadaic acid, dinophysistoxin-1, and dinophysistoxin-3 (that is, 7-O-acyl-dinophysistoxin-1). Okadaic acid is a lipophilic compound produced by sponges belonging to Halichondria (Halichondria-okadai and Halichondria-meranodocia), and dinophysistoxin-1 is a lipophilic compound produced by Dinophysis fortii. Further, dinophysistoxin-3 is a lipophilic compound produced by converting dinophysistoxin-1 inside the shellfish. These compounds accumulate in the mesenteron glands of edible bivalves in certain seasons and regions to make the shellfish toxic. The diarrheal shellfish poison is the second most frequent type of food poisoning after blowfish in terms of number of outbreaks, but is the number one in terms of the number of victims, and therefore is a major problem in food sanitation.

Hitherto, the measurement of lethal activity using mice is adopted as the official method of examination of diarrheal shellfish poisons, but there were problems in terms of the management of the animals, the sensitivity of detection, the precision, and the specificity. On the other hand, attempts have been made to develop techniques aimed at performing the above examination with a high sensitivity, in a simple manner, and in a short time.

For example, Japanese Unexamined Patent Publication (Kokai) No. 1-96199 discloses a monoclonal antibody specific to a group of the okadaic acids and a process for production of the monoclonal antibody. However, this antibody reacts in a specific manner with okadaic acid and dinophysistoxin-1 among the diarrheal shellfish poisons, but does not react with dinophysistoxin-3. Therefore, it is unable to detect or measure the latter. Further, the above-mentioned Japanese Unexamined Patent Publication (Kokai) No. 1-96199 includes no description relating to obtaining a monoclonal antibody which can maintain its activity in the presence of an organic solvent and no suggestion thereabout.

The present inventors paid attention to the facts that the food poisoning by shellfish poisons is caused mainly by dinophysistoxin-3 in Japan and that all of the above shellfish poisons are lipophilic compounds, and thus considered that it is inevitable to use organic solvents for extracting the shellfish poison components from a sample and it is desirable to carry out an immunoreaction in the presence of an organic solvent for simplification of the procedures. Therefore, the present inventors engaged in the study to solve these problems, and successfully discovered a mouse monoclonal antibody which is specific to the main components of diarrheal shellfish poisons, that is, okadaic acid, dinophysistoxin-1 and dinophysistoxin-3 and which is resistant to organic solvents, and, in addition, discovered that when this monoclonal antibody is used, it is possible to immunologically determine diarrheal shellfish poisons quickly in a specific manner, even in the presence of an organic solvent. Therefore, the present invention relates also to a monoclonal antibody, a hybridoma secreting the monoclonal antibody, and a method of determination using the monoclonal antibody.

DISCLOSURE OF THE INVENTION

In one aspect, the present invention relates to a method for determining a lipophilic compound, characterized by using an antibody tolerant to one or more organic solvent, and carrying out an antigen-antibody reaction in the presence of one or more organic solvents. More particularly, the method of the present invention is characterized in that the lipophilic compound is immunologically determined using the antibody capable of causing an accurate antigen-antibody reaction in an organic-aqueous system or an organic system containing one or more organic solvents in an amount enough to dissolve said lipophilic compound to be examined.

In another aspect, the present invention relates to a monoclonal antibody specific to, at least, okadaic acid, dinophysistoxin-1 and dinophysistoxin-3 (that is, 7-O-acyl-dinophysistoxin-1).

Further, the present invention also relates to a hybridoma producing the monoclonal antibody and a method for immunologically determining diarrheal shellfish poisons characterized by using the monoclonal antibody.

BEST MODE FOR CARRYING OUT THE INVENTION

Figure 1:
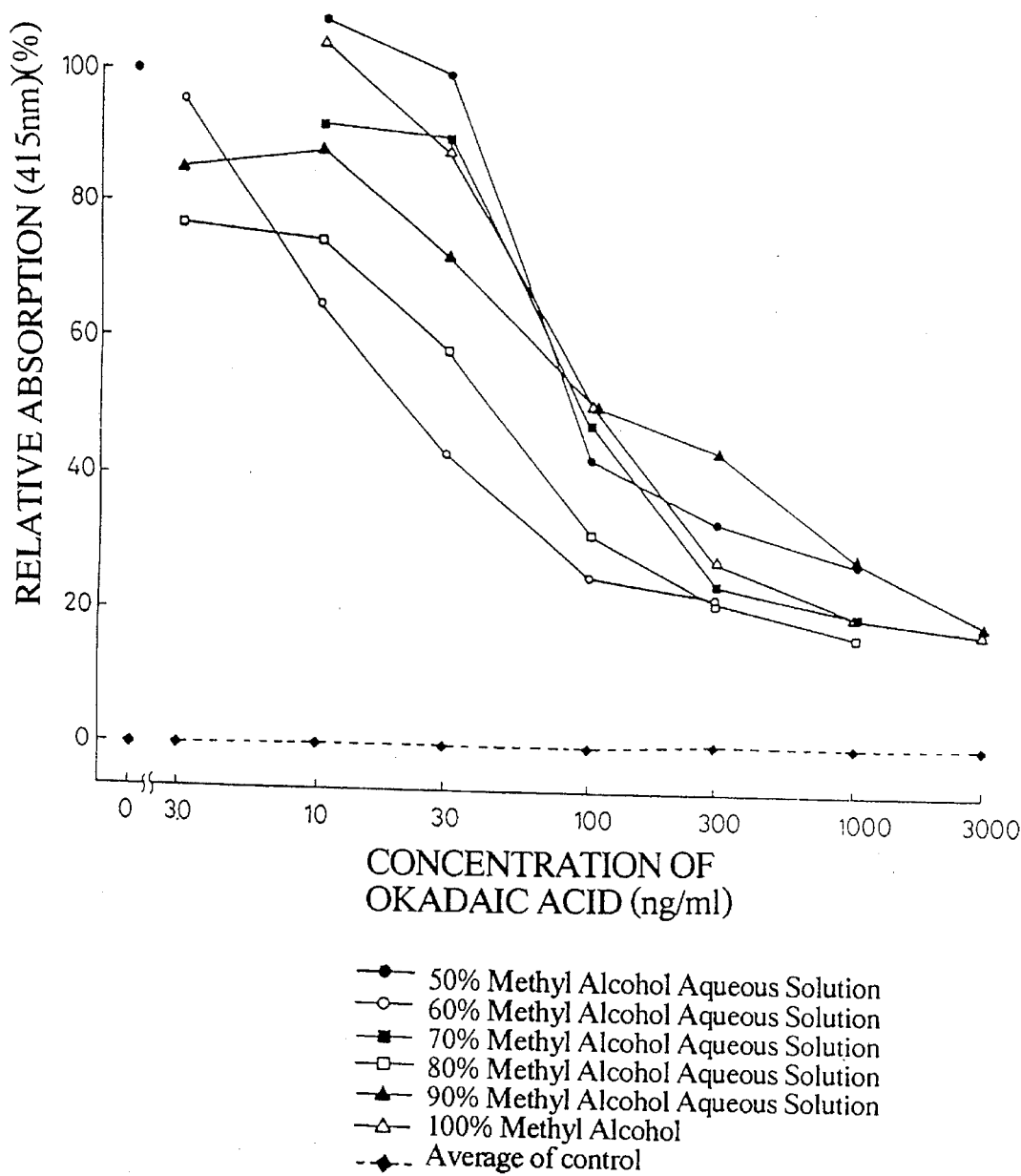
FIG. 1 is a graph showing the relationship between the concentration of okadaic acid and the absorption in an aqueous methyl alcohol containing various concentrations of methyl alcohol.
Figure 2:
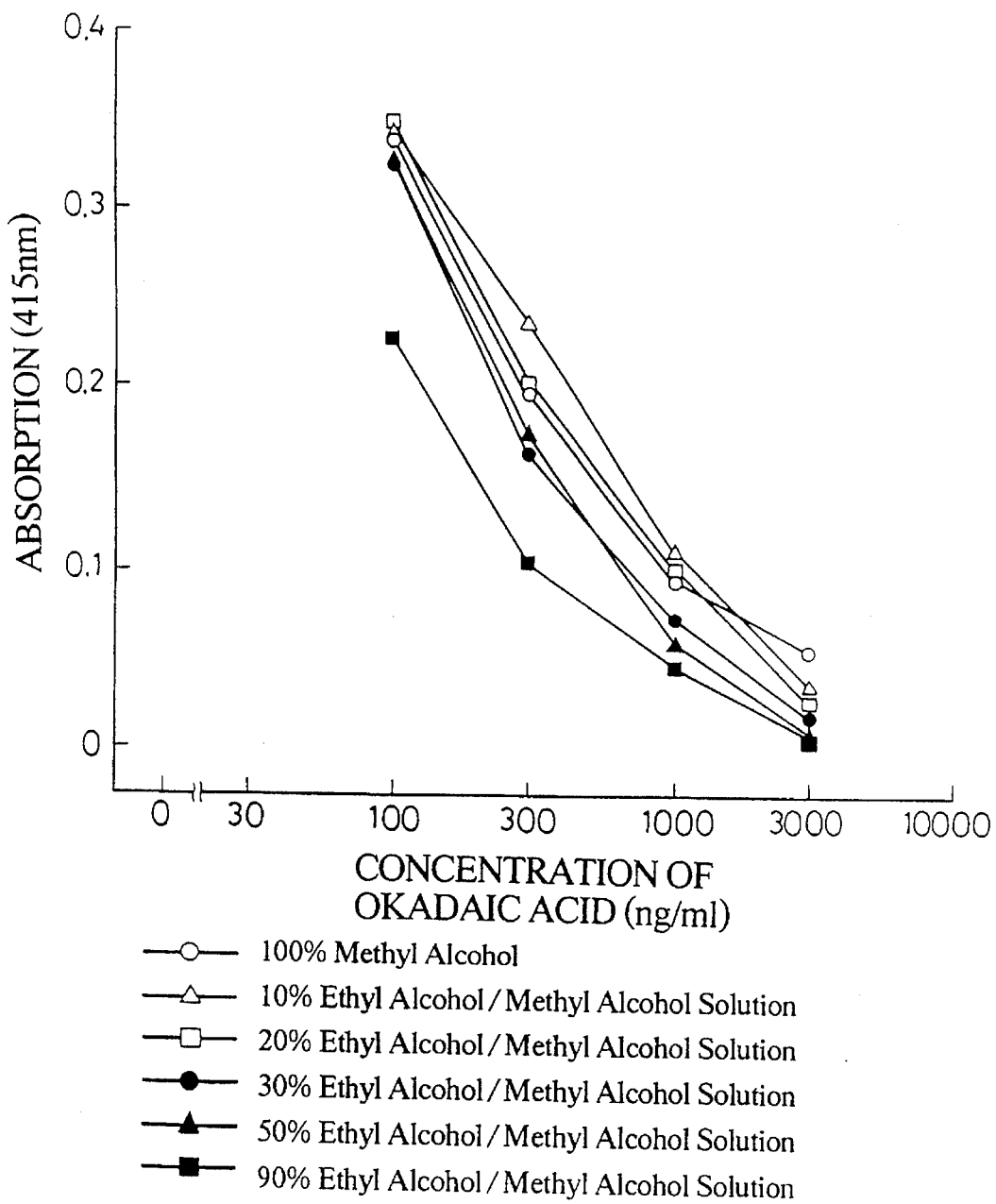
FIG. 2 is a graph showing the relationship between the concentration of okadaic acid and the absorption in a methyl alcohol containing various concentrations of ethyl alcohol.
Figure 3:
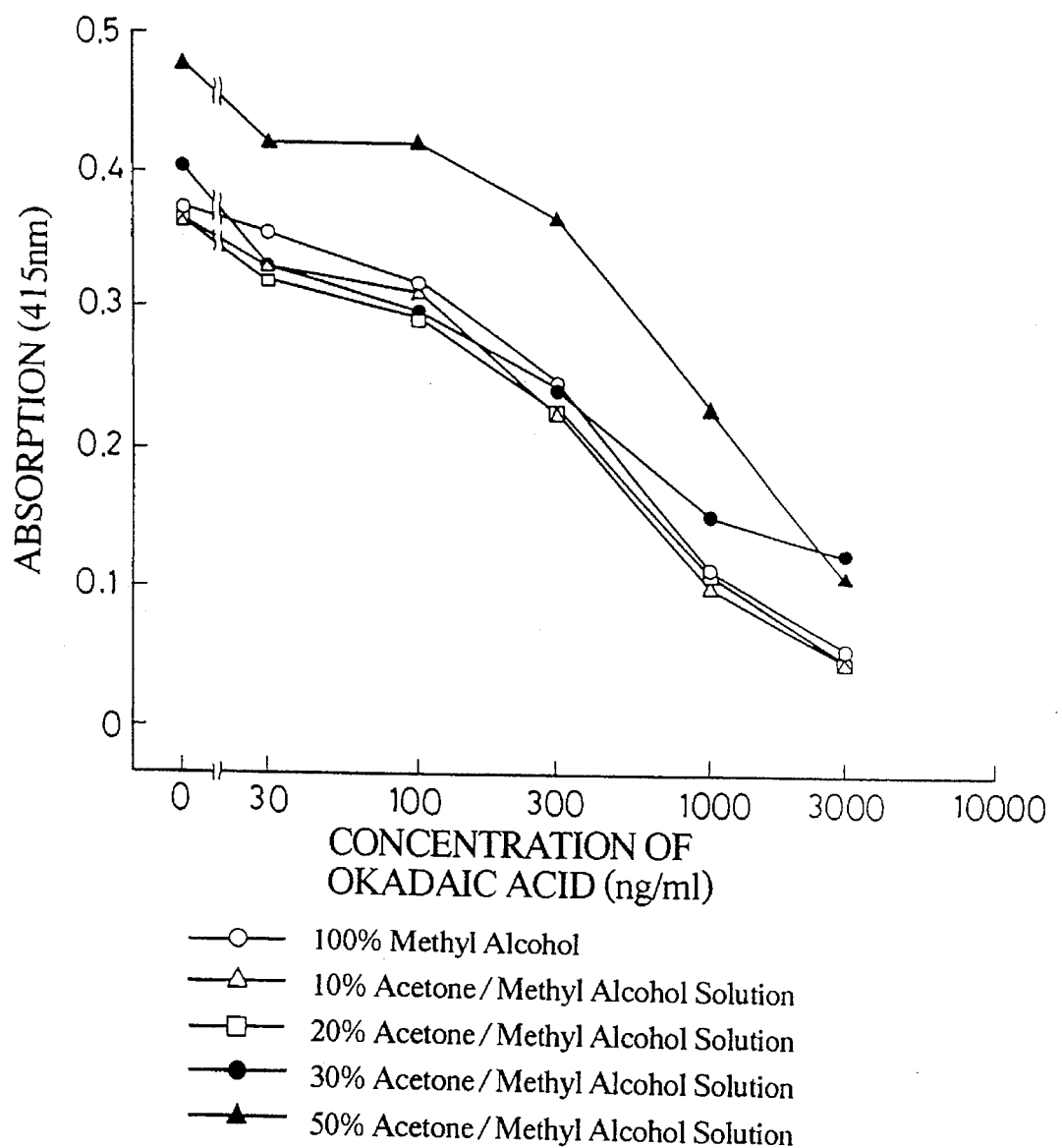
FIG. 3 is a graph showing the relationship between the concentration of okadaic acid and the absorption in a methyl alcohol containing various concentrations of acetone.
Figure 4:
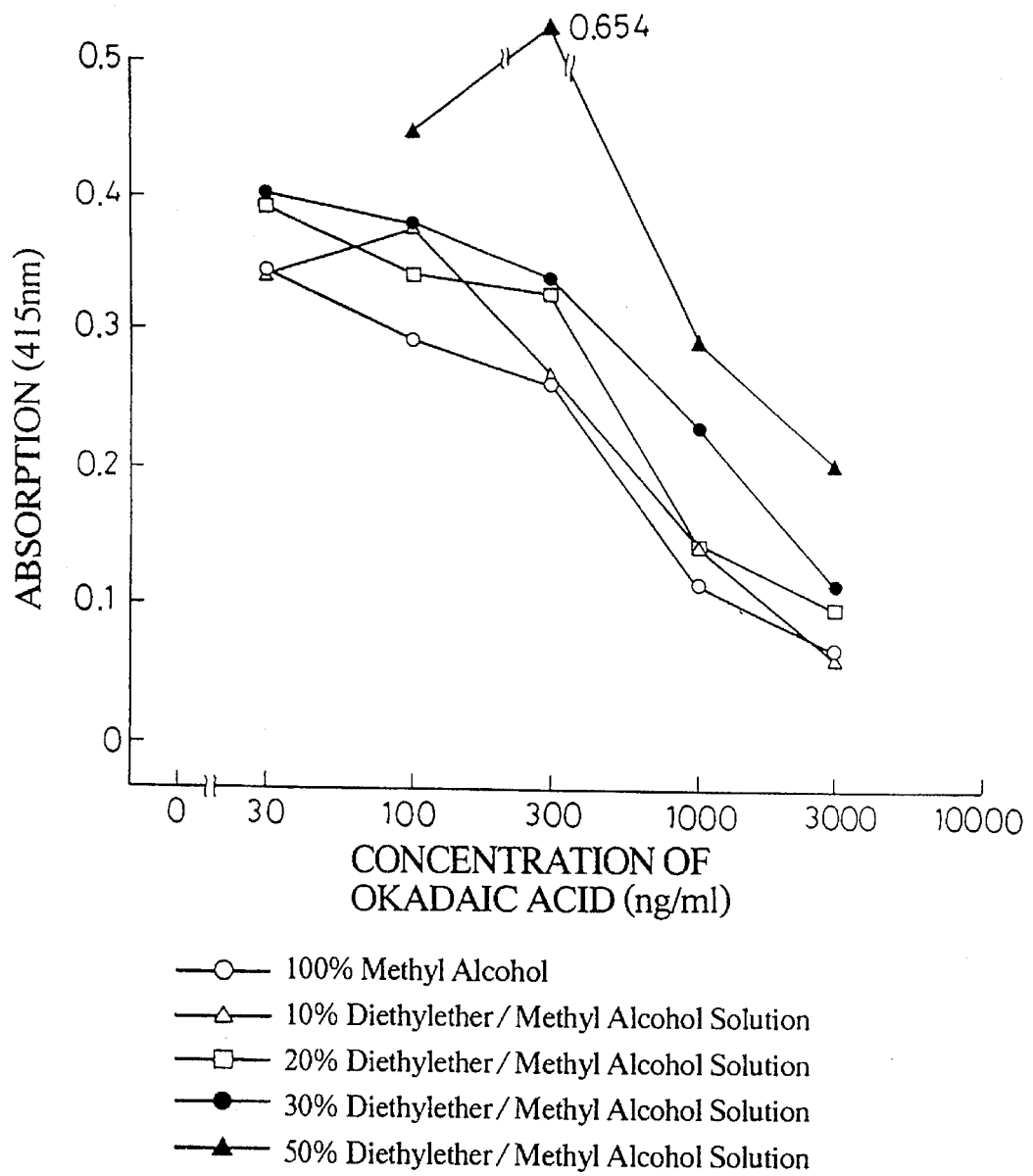
FIG. 4 is a graph showing the relationship between the concentration of okadaic acid and the absorption in a methyl alcohol containing various concentrations of diethyl ether.
Figure 5:
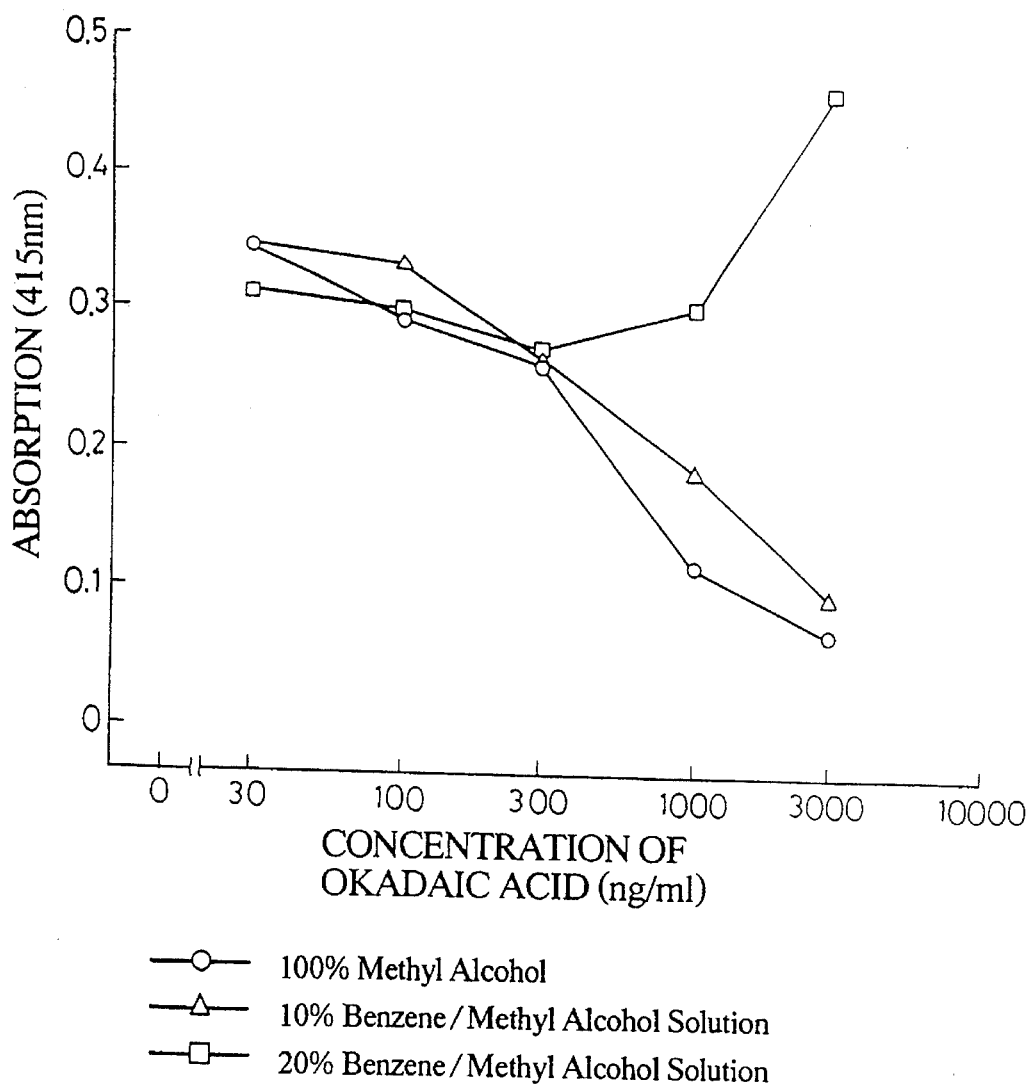
FIG. 5 is a graph showing the relationship between the concentration of okadaic acid and the absorption in a methyl alcohol containing various concentrations of benzene.

The method of determining a lipophilic compound according to the present invention can be applied to any conventionally known immunoassays, except that an antibody tolerant to one or more organic solvents is used and an antigen-antibody reaction is carried out in the presence of one or more organic solvents.

Therefore, the above method of determining a lipophilic compound specifically comprises the steps, for example:

(1) treating a sample in one or more organic solvents to prepare an organic solvent extract;

(2) bringing an antibody specific to the lipophilic compound to be examined and tolerant to one or more organic solvents, into contact with the organic solvent extract;

(3) bringing a known amount of a labeled lipophilic compound, which is the same as that to be examined, into contact with the antibody at the same time as the step (2) or after the end of the step (2);

(4) separating the labeled lipophilic compound bound to the antibody and the labeled lipophilic compound unbound to the antibody; and (5) measuring signal(s) from the label s) of one of the labeled lipophilic compound components separated at the the step (4).

The above method corresponds to that wherein the present invention is applied to those usually called the competitive and noncompetitive methods.

Further, another particular embodiment of the above method for determining a lipophilic compound comprises the steps of, for example:

(1) treating a sample in one or more organic solvents to prepare an organic solvent extract;

(2) immobilizing on an insoluble carrier a first antibody specific to the lipophilic compound to be examined and tolerant to one or more organic solvents, into contact with the organic solvent extract;

(3) bringing the organic solvent extract into contact with the immobilized first antibody of the the step (2);

(4) adding an excess amount of a labeled second antibody which is capable of binding to the lipophilic compound to be examined at a site differing from that of the first antibody; and, (5) measuring signals from the label on the second antibody bound to a complex of the first antibody and the lipophilic compound to be examined.

The above method is usually called a sandwich assay. The present invention can be widely applied to other known immunoassays.

The organic solvents which can be used in the method for determining a lipophilic compound according to the present invention are, for example, alcohols, ketones, ethers, benzene, or mixtures thereof. Further, it is possible to use anhydrous organic solvents, a mixture of various organic solvents, and further, a mixture of the organic solvent mixture with water. Furthermore, the organic solvents which can be used may be water-miscible or water-immiscible.

It is convenient to use, as the organic solvent for the present method of determination, the solvent used for the extraction of the lipophilic compound to be examined, because the antigen-antibody reaction can be carried out in the organic solvent directly after the extraction in the organic solvent. Further, it is desirable to use a water-miscible organic solvent, because the antigen-antibody reaction can be carried out in the aqueous organic solvent after extracting in an aqueous organic solution or after extracting in an organic solvent followed by dilution with water. As the water-miscible organic solvent, there may be mentioned, for example, alcohols (for example, lower alcohols having 1 to 3 carbon atoms, in particular methyl alcohol, ethyl alcohol, and isopropyl alcohol), ketones (for example, lower aliphatic ketones having 3 to 4 carbon atoms, in particular methylethylketone or acetone), or mixtures thereof.

The antibody specific to the lipophilic compounds to be examined and tolerant to one or more organic solvents can be prepared from serum of animals immunized by the lipophilic compound, but a monoclonal antibody obtained by cell fusion using the spleen cells from animals immunized by the lipophilic compound is preferred. The antibody tolerant to organic solvents is selected by adding the antibody to an aqueous organic solvent containing an organic solvent of different concentrations, followed by the addition of the lipophilic compound, and observing that the antigen-antibody reaction proceeds normally.

The lipophilic compounds which can be determined by the method of the present invention are organic compounds which are hydrophobic and which can be extracted by the organic solvents as mentioned above, and are contained in samples, for example, biological samples, in particular body fluids (for example, blood, serum, plasma, cerebral fluid, urine, and pus) of animals (in particular, human), organs, tissues, or animals or plants themselves or dried materials thereof. These lipophilic compounds are, for example, toxins (for example, diarrheal shellfish poisons) and drugs (for example, thyroid hormone). The method of the present invention is preferably used in particular for the immunoassay of toxins in marine products, residual pesticides in agricultural products, or hormones, pharmaceuticals or the like in the body fluids of animals.

In the present invention, a sample which may contain the lipophilic compound to be examined is treated by an organic solvent (if appropriate, by a mixture of an organic solvent and water) to extract the lipophilic compound to be examined (when the compound is contained in the sample). The organic solvent used for the extraction can be appropriately selected in accordance with the kind of the lipophilic compound to be examined. The obtained organic extract or aqueous organic extract is used for the next contacting step without any additional treatment or after dilution with water.

On the other hand, an antibody specific to the lipophilic compound to be examined and tolerant to the organic solvent used for the extraction of the lipophilic compound to be examined is prepared in advance by the above method. If this antibody (a first antibody in sandwich method and the organic (or aqueous organic) extract are brought into contact with each other, an antigen-antibody reaction occurs in the presence of the organic solvent, when the lipophilic compound (antigen) to be examined exists in the organic extract. The above antigen-antibody reaction may be carried out in the same manner as a usual antigen-antibody reaction, except that it is carried out in the presence of the above organic solvent. For example, the antibody is immobilized on a suitable insoluble support (for example, wells or latex particles) and reacted with the antigen in the organic extract in a specific manner.

When the method of the present invention is carried out in a manner of the competitive or noncompetitive method, it is possible to detect the lipophilic compound to be examined or determine the amount thereof, using a known amount of a labeled antigen (that is, the lipophilic compound to be examined). Further, when using the sandwich method, an excess amount of a labeled second antibody is used. For labeling the lipophilic compound to be examined, there may be used a known label, for example, radioactive isotopes (for example, $^{32}P$, $^{35}S$, $^{3}H$), enzymes (for example, peroxidase, alkaliphosphadase), vitamins (for example, biotin), fluorescent substances (for example, FITC), and chemoluminescent substances (for example, acridinium).

The labeled antigen may be added to the reaction mixture at the end of the contacting step of the antibody with the extract (namely, after the completion of the antigen-antibody reaction between the antibody and the antigen in the organic extract) [noncompetitive method] or at the beginning of the contacting step of the antibody with the organic extract (namely, simultaneously with the beginning of the antigen-antibody reaction between the antibody and the antigen in the organic extract) [competitive method]. In the noncompetitive method, antibodies unbound to the lipophilic compound to be examined in the organic extract are bound to the labeled antigens. On the other hand, in the competitive method, the known amount of labeled antigens and the unknown amount of antigens in the organic extract are bound to the antibodies competitively. In the sandwich method, the unbounded antigens are removed by washing after the first antibodies are brought into contact with the organic extract, then the labeled second antibodies are added, whereupon the labeled second antibodies bound to the complexs of the first antibodies and the antigens.

In the contacting step of the antibody and the organic solvent extract and in the adding step of the labeled antigen or the labeled second antibody, the concentration of the organic solvent is selected in view of the solubility of the lipophilic compound (antigen) and the inactivation of the label. Namely, as the concentration of the organic solvent is raised, the solubility of the lipophilic compound is increased, but some labels on the antigen will lose their activity due to the organic solvent. Therefore, the kind of the organic solvent and the concentration thereof in water are appropriately determined according to the kinds of the lipophilic compound and the label. In the noncompetitive method, it is also possible to add the labeled antigen under conditions different from the conditions where the antigen-antibody reaction is performed (for example, lowering the concentration of the organic solvent by adding water or replacing completely with an aqueous system). On the other hand, in the competitive method, the labeled antigen is added simultaneously with the beginning of the antigen-antibody reaction, so it is necessary to ensure that the label does not suffer from the inactivation due to the organic solvent present in the reaction system. For example, a label (such as, a fluorescent label) not affected by the organic solvent should be used, or inactivation of the label (for example, enzymes, avidin) is prevented by lowering the concentration of the organic solvent.

In the competitive and noncompetitive methods, after the reaction of the labeled antigens and antibodies is completed, the labeled antigens bound to the antibodies and the labeled antigens unbound to the antibodies are separated from each other. The separation may be carried out by, for example, filtration, centrifugation, or washing with a buffer. In the sandwich method, after the reaction between the antigens bound to the first antibodies and the labeled second antibodies is completed, the labeled second antibodies unbound to the antigens bound to the first antibodies are removed and then the signals from the labels on the labeled second antibodies bound to the antigens which have been bound to the first antibodies are measured.

The signals from one or both of the labels of the separated labeled antigens (competitive method or noncompetitive method) or the signals from the labels of the labeled second antibodies bound to the antigens which have been bound to the first antibodies (sandwich method) are measured. When measuring the signals, it is preferable to change the reaction system containing the labeled antigens to conditions desirable for the signal measurement. For example, when an enzyme and avidin are used as the labels, the reaction system is changed to an aqueous system and then a substrate is added to measure the enzyme activity. Further, when using a fluorescent or chemoluminescent substance as the label, the signals are measured under conditions not causing extinction of the light.

The monoclonal antibody, hybridoma, and immunological determination method according to the second aspect of the present invention will be explained hereinafter.

The monoclonal antibody and the hybridoma according to the present invention can be prepared by an ordinary method, for example, the method described in *Zoku Seikagaku Jikken Koza, Afeneki Seikagaku Kenkyuho* (Nihon Seikagakukai ed.). More concretely, as the immunogen, there may be used any substances bringing about a monoclonal antibody specific to okadaic acid, dinophysistoxin-1 and dinophysistoxin-3, but in particular, it is preferred to use okadaic acid, dinophysistoxin-1 and dinophysistoxin-3, and salts thereof, and further the biopolymer carriers (for example, bovine serum albumin or immunoglobulin) bonded therewith. These immunogen solutions are used to immunize mammals (for example, mice, rats, rabbits, goats or horses) by the in vivo immunization method. For example, the immunogen solution is emulsified by mixing with an equal amount of Freund's complete adjuvant or incomplete adjuvant and administered subcutaneously to mice (a first immunization). The same procedures are repeated at 2 to 4 week-intervals for several other immunizations. After several days from the final immunization, the spleens are removed from the mice aseptically and crushed by a stainless steel mesh or the like to prepare spleen cells for use in the cell fusion step.

Various myeloma cells of known strains may be used as the counterpart of cell fusion. Examples of the myeloma cells are p3 (p3/x63-Ag8) (*Nature*, 256, 495–497 (1975)), p3-U1 (*Current Topics in Microbiology and Immunology*, 81; 1–7 (1978)), NS-1 (*Eur. J. Immunol.*, 6; 511–519 (1976)), MPC-11 (Cell, 8; 405–415 (1976)), SP2/0 (*Nature*, 276; 269–270 (1978)), FO (*J. Immunol. Meth.*, 35; 1–21 (1980)), x63.6.55.3 (*J. Immunol.*, 123; 1548–1550 (1979)), S194 (*J. Exp. Med.*, 148; 313–323 (1978)), or R210 in rats (*Nature*, 277; 131–133 (1979)).

The cell fusion may be carried out by ordinary methods. For example, a known fusion promotor (polyethyleneglycol etc.) and optionally an auxiliary agent (dimethyl sulfoxide etc.) may be used. The ratio of the cells involved in cell fusion may be the same as in the ordinary methods. For example, the spleen cells may be used in an amount of about 1 to 10 times the amount of the myeloma cells. As the fusion medium, for example, the Delbecco modified Eagle's medium (DMEM) containing 40% (w/v) polyethyleneglycol may be used. The fusion is carried out by thoroughly mixing the immunized spleen cells and myeloma cells in the above medium.

Then, a selecting medium (for example, HAT medium) is used to remove the cells other than the hybridomas. The target hybridomas are selected by detecting the antibodies (i.e., the monoclonal antibodies specific to all of okadaic acid, dinophysistoxin-1 and dinophysistoxin-3) in the cultured medium of hybridoma by, for example, the ELISA method. In particular, when selecting hybridoma producing a monoclonal antibody tolerant to organic solvents (preferably to water-miscible organic solvents), the antibodies are added to aqueous organic solutions containing the various concentrations of an organic solvent or an anhydrous organic solvent. Then, the diarrheal shellfish poison is added to ascertain if the antigen-antibody reaction proceeds normally, whereby a hybridoma producing a monoclonal antibody tolerant to organic solvents is selected.

The resulting hybridoma of the present invention which secrets the target monoclonal antibodies can be successively cultured in an ordinary medium and can be stored for a long term in liquid nitrogen or the like. As the medium for culturing the hybridoma, any medium suitable for the cultivation of hybridoma may be used. For example, a medium comprising the DMEM including bovine fetal serum, L-glutamin, L-pyruvic acid, and antibiotics (penicillin G and streptomycin) is used. The hybridoma is preferably cultivated in the medium under a 5% $CO_2$ concentration at 37° C. for about 3 days in the case of in vitro cultivation, or for about 14 days in the case of in vivo cultivation, for example, in the abdominal cavity of mice.

The target monoclonal antibody can be separated and purified from the cultured medium prepared by an ordinary method or from the ascites of suitable mammals (for example, mice or rats) to which the hybridoma has been administered. When separating and purifying the monoclonal antibody from the cultured medium or the ascites of mice, it is possible to use the methods generally applied to the isolation and purification of protein. As examples thereof, there may be mentioned the ammonium sulfate salting out, ion exchange chromatography, molecular sieve column chromatography using molecular sieve gel, affinity column chromatography using protein A or protein G-bonded polysaccharides or the like, dialysis, lyophilization, or the like.

The method of determination of diarrheal shellfish poisons according to the present invention is performed using the monoclonal antibody of the present invention (that is, a monoclonal antibody specific to all of okadaic acid, dinophysistoxin-1 and dinophysistoxin-3), so it is possible to determine diarrheal shellfish poisons without exception. Further, in a preferable embodiment of the method of determination of diarrheal shellfish poisons of the present invention, a monoclonal antibody tolerant to organic solvents is used, so it is possible to make the antigen-antibody reaction proceed accurately in an organic system or an aqueous organic system containing an organic solvent enough to dissolve the diarrheal shellfish poisons to be examined.

The method for determining diarrheal shellfish poisons of the present invention can be applied to the conventionally known immunoassays without any modification, except that a monoclonal antibody specific to all of okadaic acid, dinophysistoxin-1 and dinophysistoxin-3 is used, and that an antibody tolerant to an organic solvent(s) is preferably used (therefore, the antigen-antibody reaction is performed in the presence of an organic solvent). Therefore, the method for determining the diarrheal shellfish poisons of the present invention can be widely applied to known immunoreaction determination methods, such as the competitive and non-competitive methods, and the sandwich method, using "an antibody specific to diarrheal shellfish poisons and tolerant to the organic solvent(s)" as "an antibody specific to the lipophilic compound to be examined and tolerant to organic solvent(s)" in the above method for determining a lipophilic compound.

The organic solvent used in the method of determination of diarrheal shellfish poisons of the present invention may be alcohols or ketones as in the above method for determining a lipophilic compound, and is a solvent which is used when extracting the diarrheal shellfish poisons to be examined from the sample. Further, it is preferable to use a water-miscible organic solvent in the same manner as in the above method for determining a lipophilic compound.

When actually carrying out the method of determination of diarrheal shellfish poisons of the present invention, first the mesenteron gland sample of an edible bivalve is extracted by the above organic solvent(s). The resulting extract is used in the next contacting step without any further treatment, or after diluting with water. On the other hand, for example, a mouse monoclonal anti-okadaic acid antibody tolerant to water-miscible organic solvent(s) is prepared in advance by the method as mentioned above. When the antibody (the first antibody in the sandwich method) is brought into contact with the above-mentioned organic solvent extract, an antigen-antibody reaction occurs in the presence of the organic solvent, if there is a diarrheal shellfish poison (antigen) present in the organic solvent extract. This antigen-antibody reaction may be performed in the same manner as in the usual antigen-antibody reaction, except that the reaction is performed in the presence of an organic solvent. For example, the antibody is immobilized onto an appropriate insoluble support (wells or latex particles) and then reacted with the antigen in the organic solvent extract in a specific manner.

When carrying out the method of determination of diarrheal shellfish poisons of the present invention by the competitive or noncompetitive method or by the sandwich method, it is possible to use reagents and procedures similar to those of the above method determining lipophilic compounds.

EXAMPLES

The present invention now will be further illustrated by, but is by no means limited to, the following examples.

Example 1: Preparation of Monoclonal Antibody-Producing Hybridoma

Okadaic acid (2 mg) (Wako Pure Chemical Industries) (hereinafter referred to as OA; a kind of diarrheal shellfish poison), N-hydroxysuccinimide (0.31 mg) and N,N-dicyclohexylcarbodiimide (0.57 mg) were dissolved in 120 µl of dimethylformamide (hereinafter referred to as DMF) and reacted at room temperature for 2 hours. The resulting reaction liquid was divided into two parts. To 39 µl of one part of the reaction liquid, 1.5 mg of human IgG was added. To 81 µl of the other part of the reaction liquid, 1.9 mg of bovine serum albumin (hereinafter referred to as BSA) was added to be dissolved. Then, each of the resulting solutions was reacted at room temperature for further 2 hours, respectively. Finally, each of the resulting reaction liquids was treated by gel filtration, using a Sephadex G-25 column equilibrated by PBS (pH 7.4). The resulting OA-human IgG and OA-BSA were dissolved in a physiological saline at concentrations of 0.826 mg/ml and 1.04 mg/ml. The OA-human IgG was used as an immunogen, and the OA-BSA was used as an antigen for analysis.

To 300 µl of the OA-IgG solution, an equal amount of Freund's complete adjuvant was added. The whole was thoroughly mixed to prepare a homogeneous sol. 200 µl of the sol was administered inside the abdominal cavity of female mice (4 weeks' old; A/J). After 2 months, a further antigen sol prepared similarly to the above was administered inside the abdominal cavity in the same amount.

The spleens of the mice with the high titers of the anti-OA antibody in the serum were removed, washed three times in petri dishes by a T-2 medium containing 5% bovine fetal serum, then scratched by a syringe needle and squeezed to prepare a suspension of single cells. The single cell suspension was filtered by a mesh to remove the large solids. To the resulting filtrate, mouse myeloma cells P3X-63-Ag8-6.5.3 was mixed for a ratio of 1:5 with respect to the cell count (myeloma cells:spleen cells), and the whole was centrifuged (300×g, 4 minutes) to collect the cells. Then, the precipitated cells were resuspended in a T-3 medium not containing serum, and centrifuged under the same conditions. The centrifugation tube was tapped by a finger to agitate the precipitate, then 1 ml of a 50% polyethyleneglycol (molecular weight 1,500) solution preheated to 37° C. was added slowly over 60 seconds while rotating the centrifugation tube. The cell fusion was terminated by adding T-3 medium not containing serum to the centrifugation tube in which the cell fusion was progressing. In this procedure, the addition of the T-3 medium was divided into three times (first 3 ml of the medium, then 9 ml of the medium, and finally 38 ml of the medium, over 30 seconds, respectively). After the addition of the medium was completed, the mixture was held at 37° C. for 2 minutes, then at room temperature for 8 minutes, then was centrifuged. The obtained cells were suspended in a T-2 medium to adjust a cell count of $2\times10^6$/ml. The cell suspension was poured in a 96-well plastic plate in amounts of 100 µl/well, then was cultured at 37° C. in a 5% carbon dioxide-95% air gas phase. After 24 hours, T-4 medium was added in an amount of 100 µl/well and the cultivation was continued for 10 to 14 days under the same conditions. The activity of the anti-OA antibodies in the culture liquid was examined, and the cells in the wells which showed the production of the target antibodies were used for cloning hybridoma by the limiting dilution method using an HT medium by a 24-well plastic plate. As a result of the cloning, 14 clones of hybridoma (fused cell) producing the anti-OA antibody were obtained.

Example 2: Preparation of Monoclonal Antibody

Each of the 14 hybridoma clones selected in Example 1 was cultured in Celgrosser-H (for hybridoma; a tissue cultivation serum-free medium; Sumitomo Seiyaku) containing 2.5 µg/ml each of penicillin, streptomycin, and Fungizone. The resulting cells were suspended in the same media and cultured at 37° C. in a 5% carbon dioxide-95% air gas phase, using a Hillipore Dynacell Culture System (Millipore Co.) to produce the anti-OA antibodies. After the cultivation was completed, the culture liquid was treated by ammonium sulfate fractionation. The resulting monoclonal antibody was dialyzed after dissolved in a 5 mM tris-hydrochloride buffer (pH 7.5) containing 0.9% NaCl.

Example 3: Selection of Honoclonal Antibody

The anti-OA monoclonal antibodies produced by the 14 hybridoma clones were used to prepare ELISA plates. Namely, the anti-OA monoclonal antibodies prepared in Example 2 were dissolved in 0.083M borate buffered saline (pH 8.0) (hereinafter referred to as BBS) in a concentration of 10 µg/ml, and poured on a 96-well plate in amounts of 100 µl/well. The plate was allowed to stand at room temperature for 1 hour to immobilize the antibodies. The wells were washed three times with 250 µl of BBS, then 250 µl of gelatin solution (10 mg/ml) dissolved in BBS was poured into the wells and allowed to stand at room temperature for 1 hour for blocking.

On the other hand, OA was dissolved in known concentrations in a series of methyl alcohol aqueous solutions prepared by adjusting the concentrations of methyl alcohol with water from 0% (water) to 100% (absolute alcohol) in 10% increments. Thus, OA standard alcoholic aqueous solutions were prepared.

To the wells of the above ELISA plates, 100 μl of the above OA standard alcohol aqueous solutions were added. The plates were allowed to stand at room temperature to allow the antigen-antibody reaction to proceed. After 1 hour, the wells were washed five times with 250 μl of BBS. Then, 100 μl of solutions (BBS containing 1.0% gelatin) containing 25 to 100 ng/ml of OA labeled with peroxidase (hereinafter referred to as OA-POD) were added to the wells and allowed to stand at room temperature for 1 hour. Thereafter, the plates were washed five times with 250 μl of BBS, then 100 μl of substrate solutions [prepared by diluting 100 μl of a solution of 3,3',5,5'-tetramethylbenzidine (100 mg) dissolved in DMF (10 ml) with 9.9 ml of a 0.1M sodium acetate solution (pH 5.5), then adding 15 μl of 3% hydrogen peroxide aqueous solution; hereinafter referred to as TMBZ solution] was poured into the wells and allowed to react at room temperature for 5 to 40 minutes. Then, 100 μl of 1N sulfuric acid was added to terminate the reaction. The absorption of the reaction liquid was measured at 450 nm or 415 nm by a spectrophotometer (Hitachi Spectrophotometer U-1100) and a calibration curve was prepared.

As a result, it was found that the anti-OA monoclonal antibody produced by the hybridoma OA-423 strain (hereinafter referred to as OA-423 antibody) can correctly recognize an antigen and perform a normal antigen-antibody reaction even in 100% methyl alcohol. The hybridoma OA-423 was domestically deposited in the Fermentation Research Institute of the Agency of Industrial Science and Technology of the Japanese Ministry of International Trade and Industry (address: 1–3, Higashi 1-chome, Tsukuba-shi, Ibaragi 305, Japan) on Oct. 25, 1991 (FERH P-12585), and was transferred to international deposition on Jul. 27, 1992 (FERN BP-3943).

The anti-OA monoclonal antibody (OA-423 antibody) produced by the hybridoma OA-423 strain correctly recognizes an antigen and performs a normal antigen-antibody reaction in 0% (0.083M borate physiological saline) to 100% methyl alcohol. Further, the anti-OA monoclonal antibodies produced by the hybridoma OA-127 strain and the 227 strain correctly recognized antigens and performed normal antigen-antibody reactions in an aqueous solution containing not more than 50% methyl alcohol.

The immunoglobulin class of the OA-423 antibody was examined by the ELISA, using mouse biotin-labeled antibodies for discriminating Ig subclass (Ig, IgM, IgG1, IgG2a, IgG2b, IgG3, IgA, λ-type L chain, and κ-type L chain), to find IgG1κ.

Example 4: Determination of Okadaic Acid

A calibration curve was prepared by the procedure same as that in Example 3, using standard OA solutions prepared by dissolving various known concentrations of OA in 50%, 60%, 70%, 80% and 90% methyl alcohol aqueous solutions and 100% methyl alcohol, and ELISA plates of OA-423 antibody prepared under the conditions described in Example 3. Namely, 10 μg/ml of OA-423 antibody was immobilized in wells and 50 ng/ml of OA-POD was used to perform an enzyme reaction at 22.5° C. to 26.5° C. for 8 to 20 minutes. For a control test, mouse IgG1 (10 μl/ml) was used. The results are shown in FIG. 1.

It is manifest from FIG. 1 that the OA-423 antibody performs a normal antigen-antibody reaction with OA even in 100% methyl alcohol, and therefore, an assay could be performed using a methyl alcohol extract of OA without any further treatment.

Example 5: Determination of Okadaic Acid

Calibration curves were prepared by the procedure same as that in Example 3, using standard OA solutions prepared by dissolving various known concentrations of OA in 100% methyl alcohol or mixtures thereof with 0 to 90%, 0 to 50%, or 0 to 20% of ethanol, acetone, ether, or benzene, and ELISA plates of OA-423 antibody prepared under the conditions described in Example 3. Namely, 10 μg/ml of OA-423 antibody was immobilized in wells and 50 ng/ml of OA-POD was used to perform an enzyme reaction at 22° C. to 25° C. for 20 to 30 minutes. The results are shown in FIGS. 2 to 5.

Example 6: Determination of Diarrheal Shellfish Poisons by Noncompetitive Method Standard products of OA, dinophysistoxin-1 (hereinafter referred to as DTX1) and dinophysistoxin-3 (7-O-palmytoyl-DTX1) (hereinafter referred to as DTX3) were measured by a noncompetitive method. The ELISA plates used were prepared, using the OA-423 antibody under the conditions described in Example 3. In view of the of extraction procedure from the actual samples, the standard solutions for samples were prepared by once drying to a solid the 100% methyl alcohol solution of the diarrheal shellfish poisons and then redissolving in BBS containing various concentrations of methyl alcohol.

ELISA plates carrying the OA-423 antibody were used to measure the standard products of OA, DTX1 and DTX3 by the noncompetitive method described in Example 3. The examination was performed for 11 steps of the methyl alcohol concentrations in 10% increments from 0% to 100% and calibration curves were prepared. The results are shown in FIGS. 6 to 11.

Figure 6:
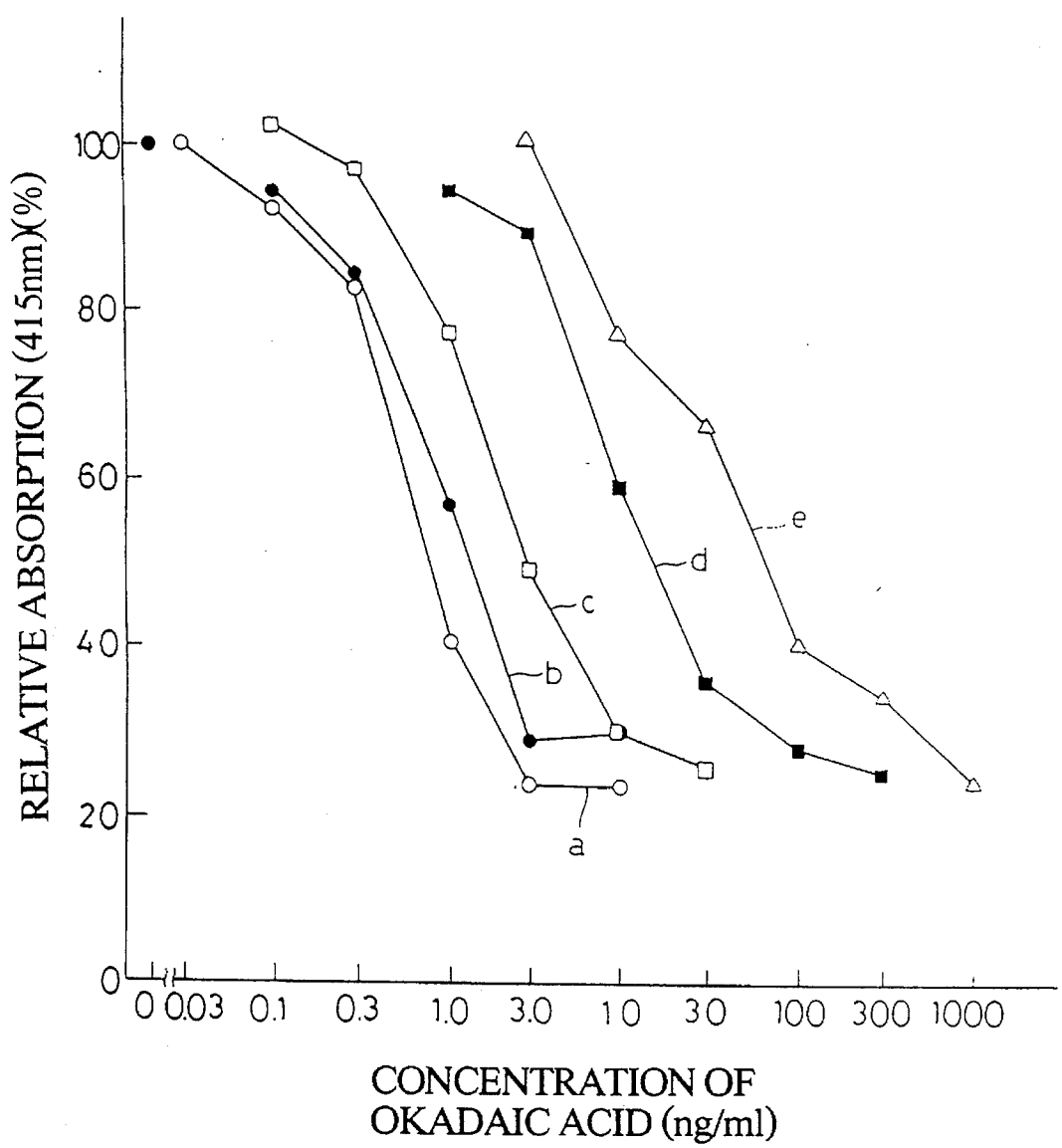
FIG. 6 is a graph showing a calibration curve in the case of measuring okadaic acid in aqueous solutions containing 0 to 40% methyl alcohol by the noncompetitive method.
Figure 7:
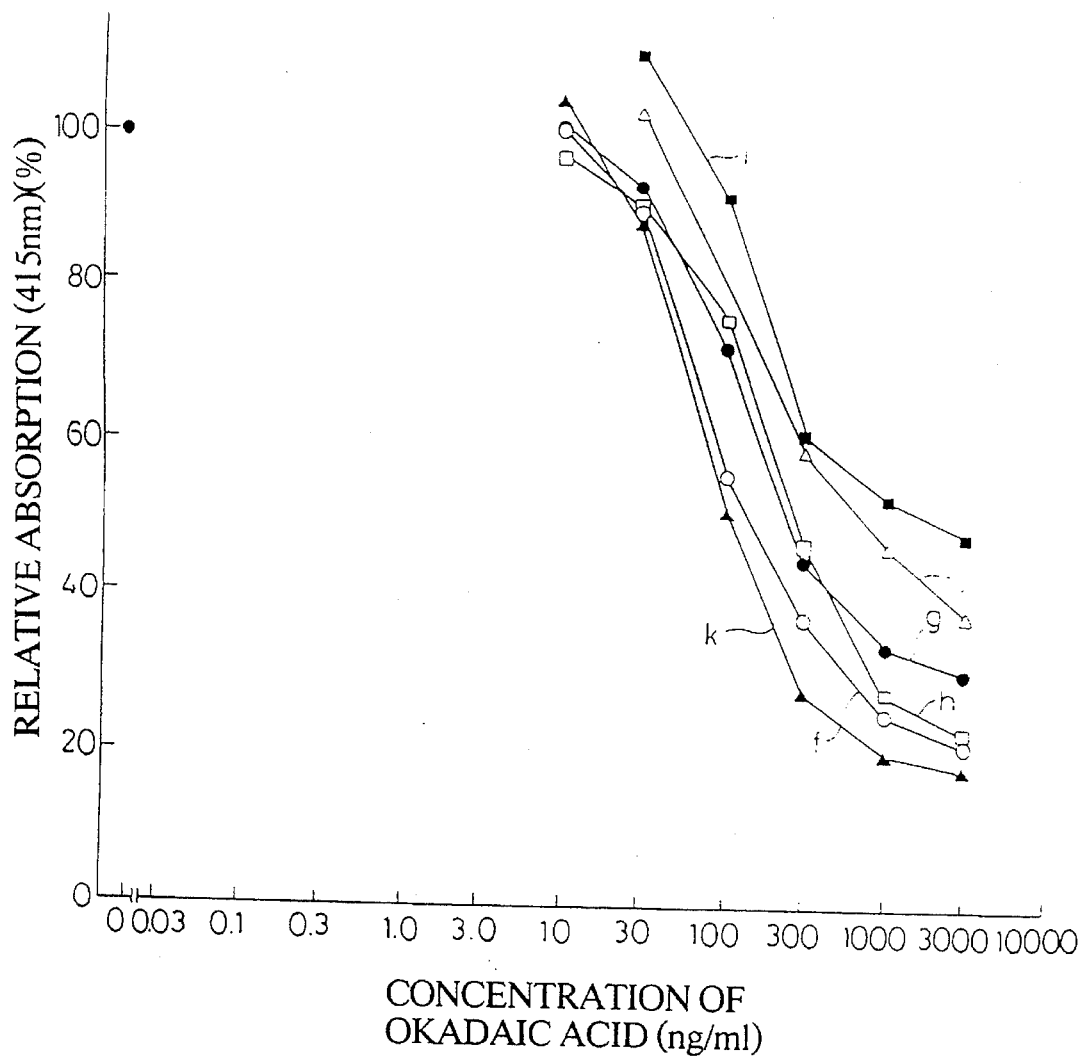
FIG. 7 is a graph showing the calibration curve in the case of measuring okadaic acid in aqueous solutions containing 50 to 100% methyl alcohol by the noncompetitive method.

In the range of the methyl alcohol concentration of not more than 10%, the methyl alcohol concentration does not affect the measurement results in the noncompetitive method of the OA, and the quantitative determination of OA can be effected in the range of 0.1 to 3.0 ng/ml, with a good sensitivity. However, if the methyl alcohol concentration is raised to 20%, the sensitivity is lowered and the range of the quantitative determination becomes 0.3 to 10 ng/ml. If the methyl alcohol concentration becomes over 40%, almost no reduction in the sensitivity is observed and the range of the quantitative determination is 3.0 to 1000 ng/ml (FIG. 6). However, if the methyl alcohol concentration becomes over 50%, there is a tendency of a higher background value (FIG. 7).

Figure 8:
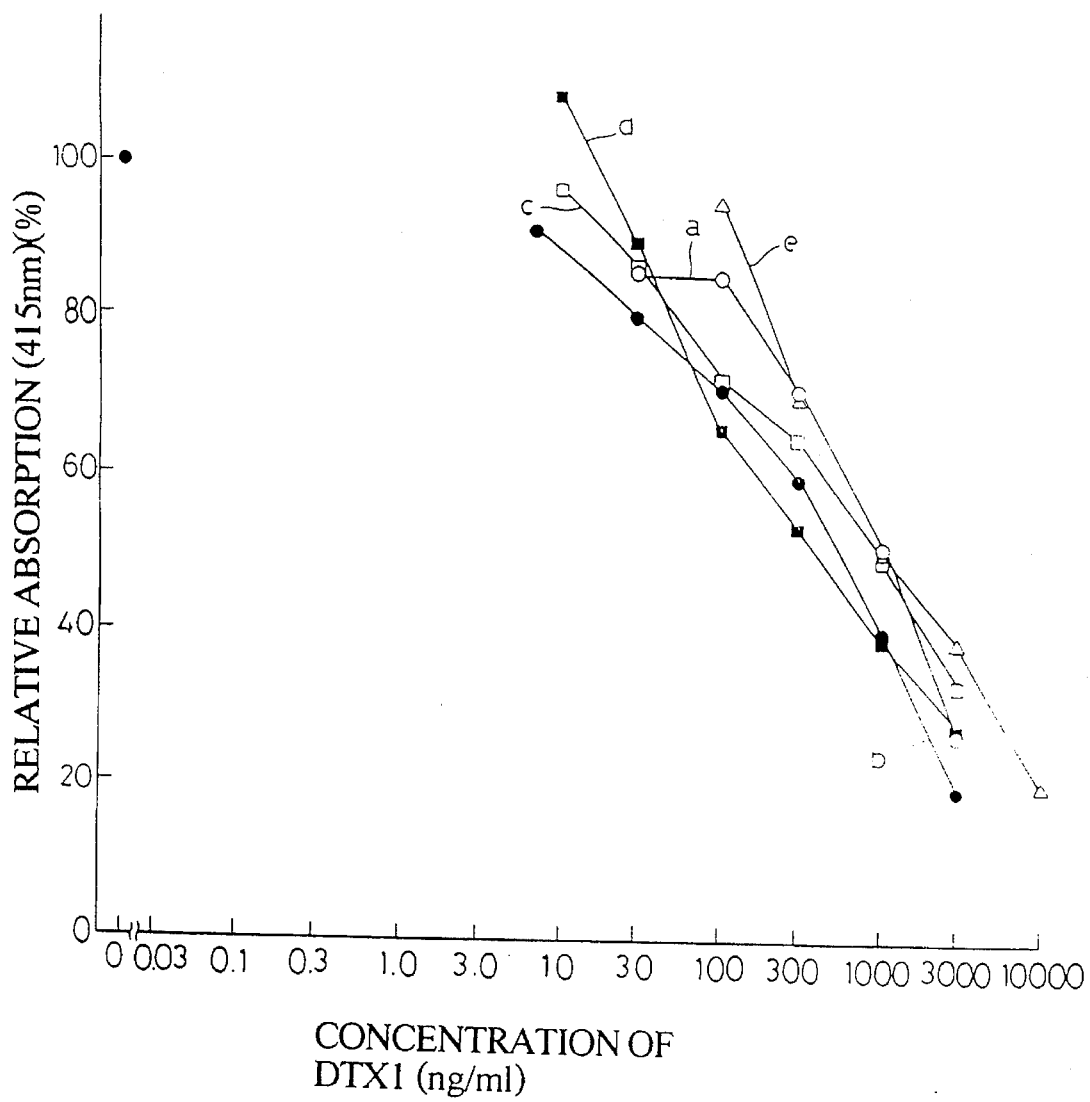
FIG. 8 is a graph showing the calibration curve in the case of measuring dinophysistoxin-1 in aqueous solutions containing 0 to 40% methyl alcohol by the noncompetitive method.
Figure 9:
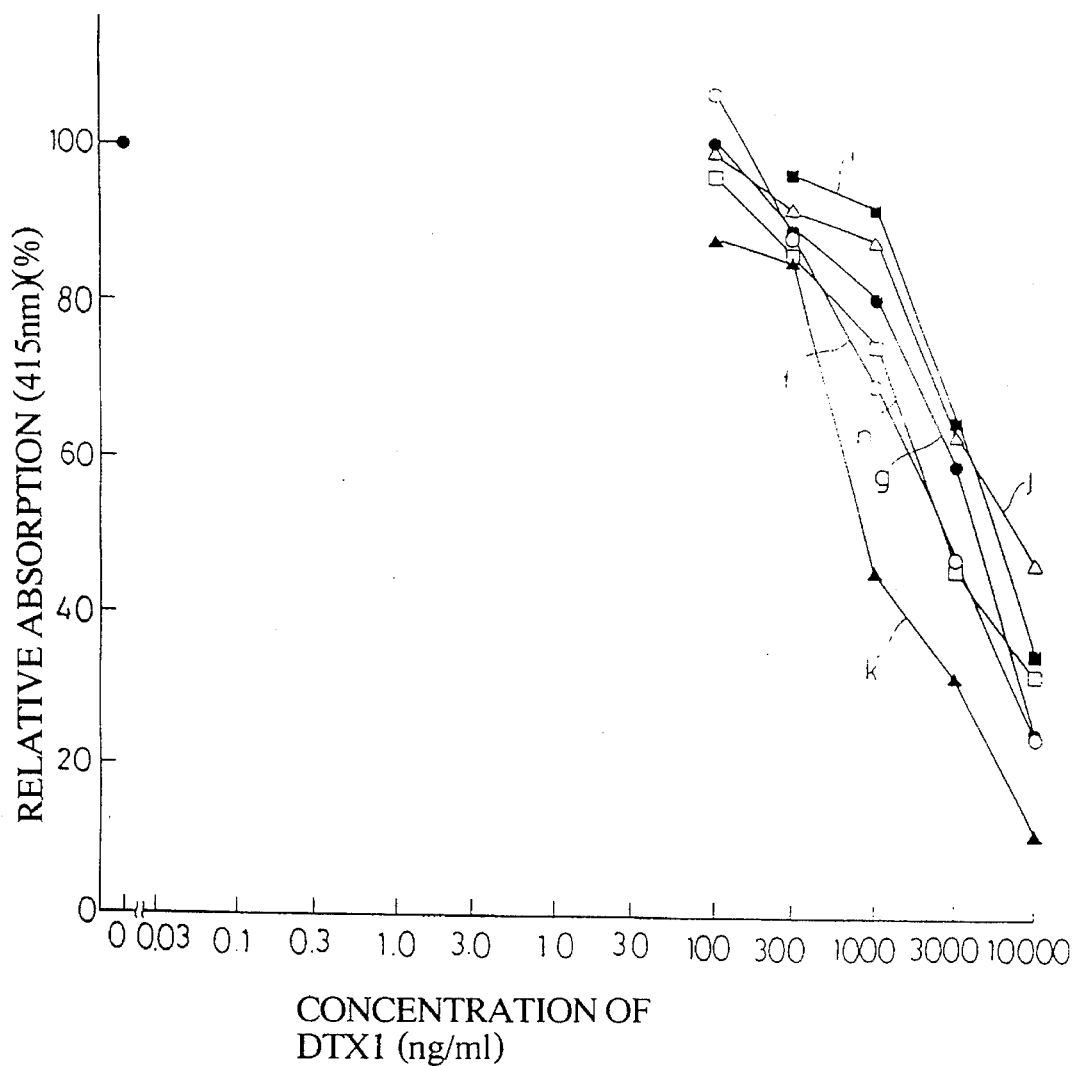
FIG. 9 is a graph showing the calibration curve in the case of measuring dinophysistoxin-1 in aqueous solutions containing 50 to 100% methyl alcohol by the noncompetitive method.

As shown in the results of measurement of DTX1, the sensitivity of DTX1 is lower than OA. Even if the methyl alcohol concentration is not more than 40%, the range of the quantitative determination is 10 to 3,000 ng/ml or 10 to 10,000 ng/ml (FIG. 8). If the methyl alcohol concentration is raised up over 50%, the range of the quantitative determination becomes 100 to 10,000 ng/ml, and, a further reduction of sensitivity cannot be observed as in OA (FIG. 9).

Figure 10:
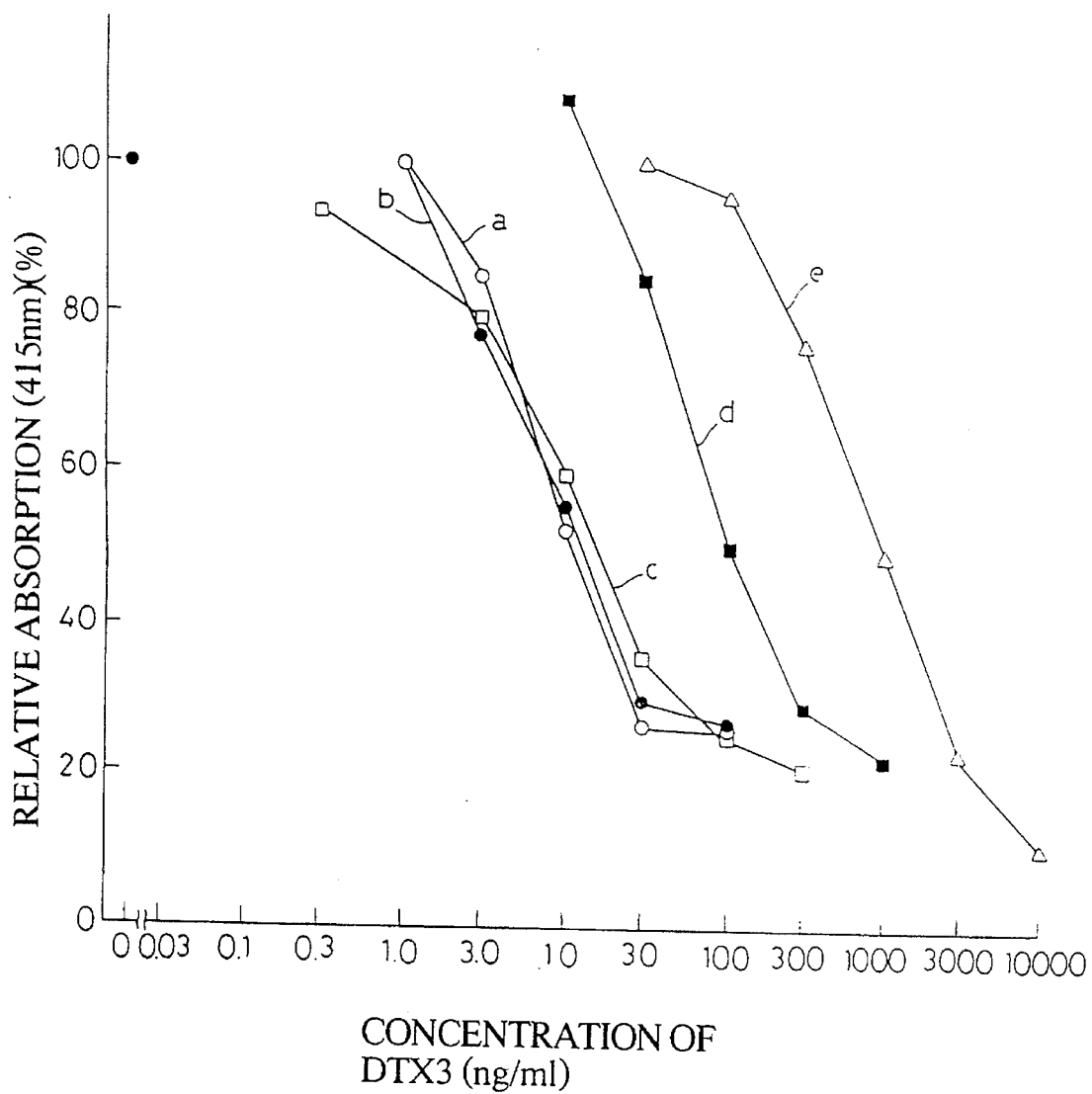
FIG. 10 is a graph showing the calibration curve in the case of measuring dinophysistoxin-3 in aqueous solutions containing 0 to 40% methyl alcohol by the noncompetitive method.
Figure 11:
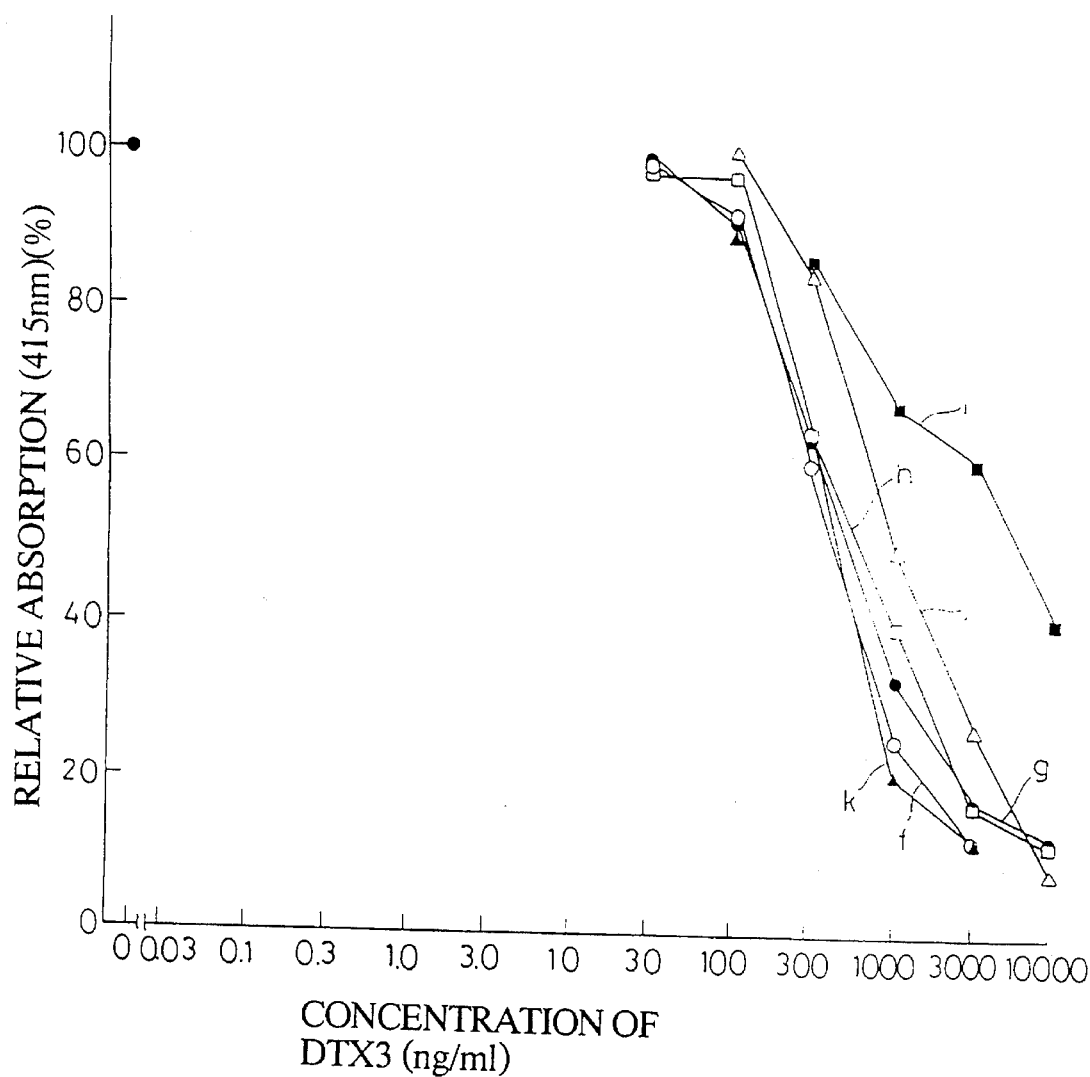
FIG. 11 is a graph showing the calibration curve in the case of measuring dinophysistoxin-3 in aqueous solutions containing 50 to 100% methyl alcohol by the noncompetitive method.

As shown in the results of measurement of DTX3, the methyl alcohol concentration in a range of not more than 20% does not affect the result, and the quantitative determination is possible in a range of 1.0 to 30 ng/ml of DTX3. The methyl alcohol concentration of over 20% affects the results of measurement. When the methyl alcohol concentration becomes up to 30%, the sensitivity becomes lowered, and the range of the quantitative determination is 10 to 300 ng/ml (FIG. 10). Further, when the methyl alcohol concentration is raised to 40% or more, the range of the quantitative determination is 100 to 3,000 ng/ml or 100 to 10,000 ng/ml (FIGS. 10 and 11). Based on the results of the above measurement for OA, DTX1 and DTX3, the reactivities of OA-423 antibody with respect to the three kinds of diarrheal shellfish poisons at the various methyl alcohol concentrations are summarized in the following Table 1. If the methyl alcohol concentration is not more than 20%, the OA-423 antibody does not react with DTX1 in the low concentration range of the shellfish poisons where the OA-423 antibody quantitatively reacts with the OA and DTX3. Therefore, it is possible to quantitatively determine only the OA and DTX3, by controlling the methyl alcohol concentration.

TABLE 1

| Methyl alcohol concentration (%) | OA | DTX1 | DTX3 |
| --- | --- | --- | --- |
| 0 | 1 | 0.0006 | 0.07 |
| 10 | 1 | 0.002 | 0.13 |
| 20 | 1 | 0.005 | 0.17 |
| 30 | 1 | 0.1 | 0.17 |
| 40 | 1 | 0.06 | 0.05 |
| 50 | 1 | 0.07 | 0.27 |
| 60 | 1 | 0.03 | 0.31 |
| 70 | 1 | 0.17 | 0.50 |
| 80 | 1 | 0.03 | 0.05 |
| 90 | 1 | 0.04 | 0.14 |
| 100 | 1 | 0.08 | 0.23 |

Example 7: Determination of Diarrheal Shellfish Poisons by Competitive Method

Figure 12:
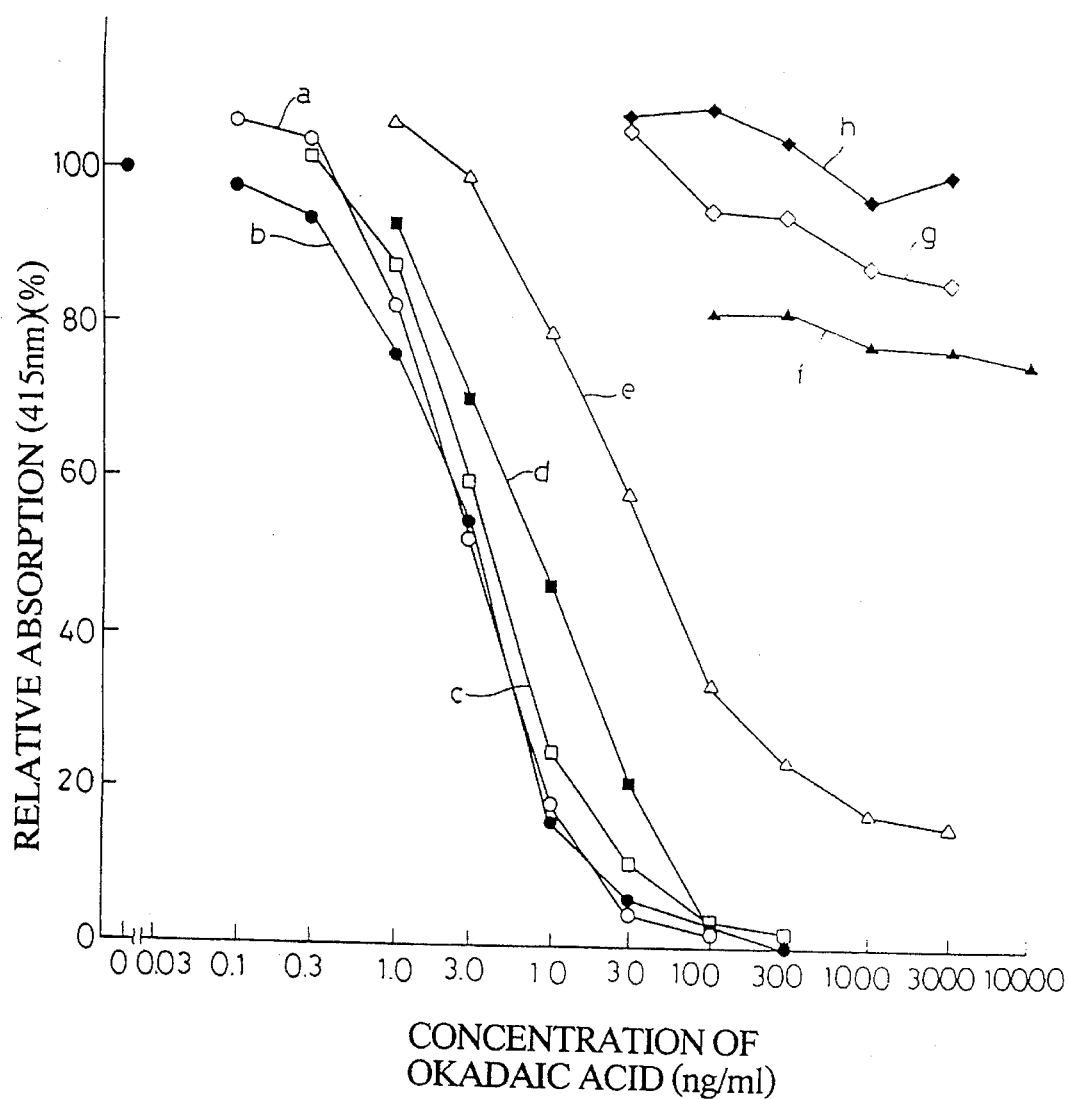
FIG. 12 is a graph showing the calibration curve in the case of measuring okadaic acid by the competitive method.
Figure 13:
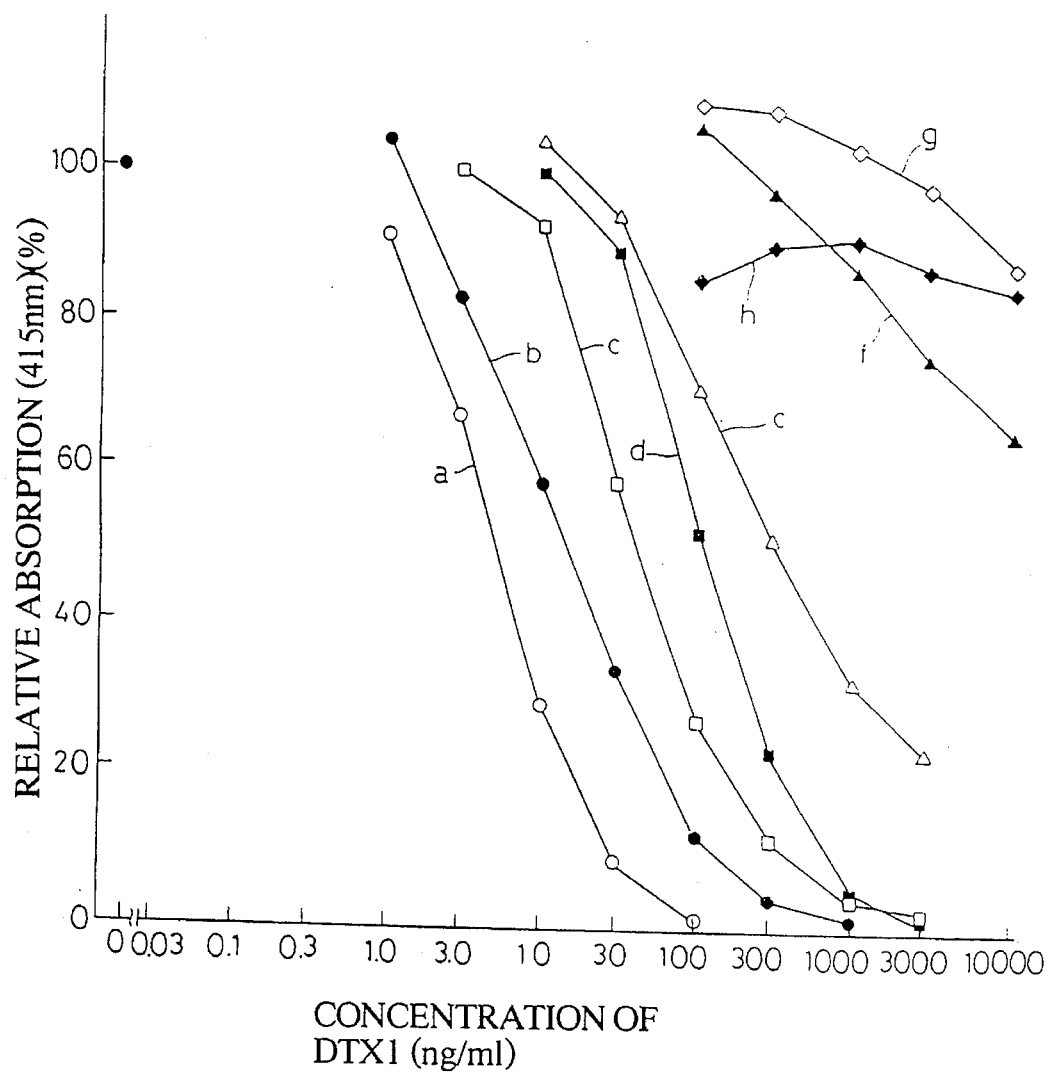
FIG. 13 is a graph showing the calibration curve in the case of measuring dinophysistoxin-1 by the competitive method.
Figure 14:
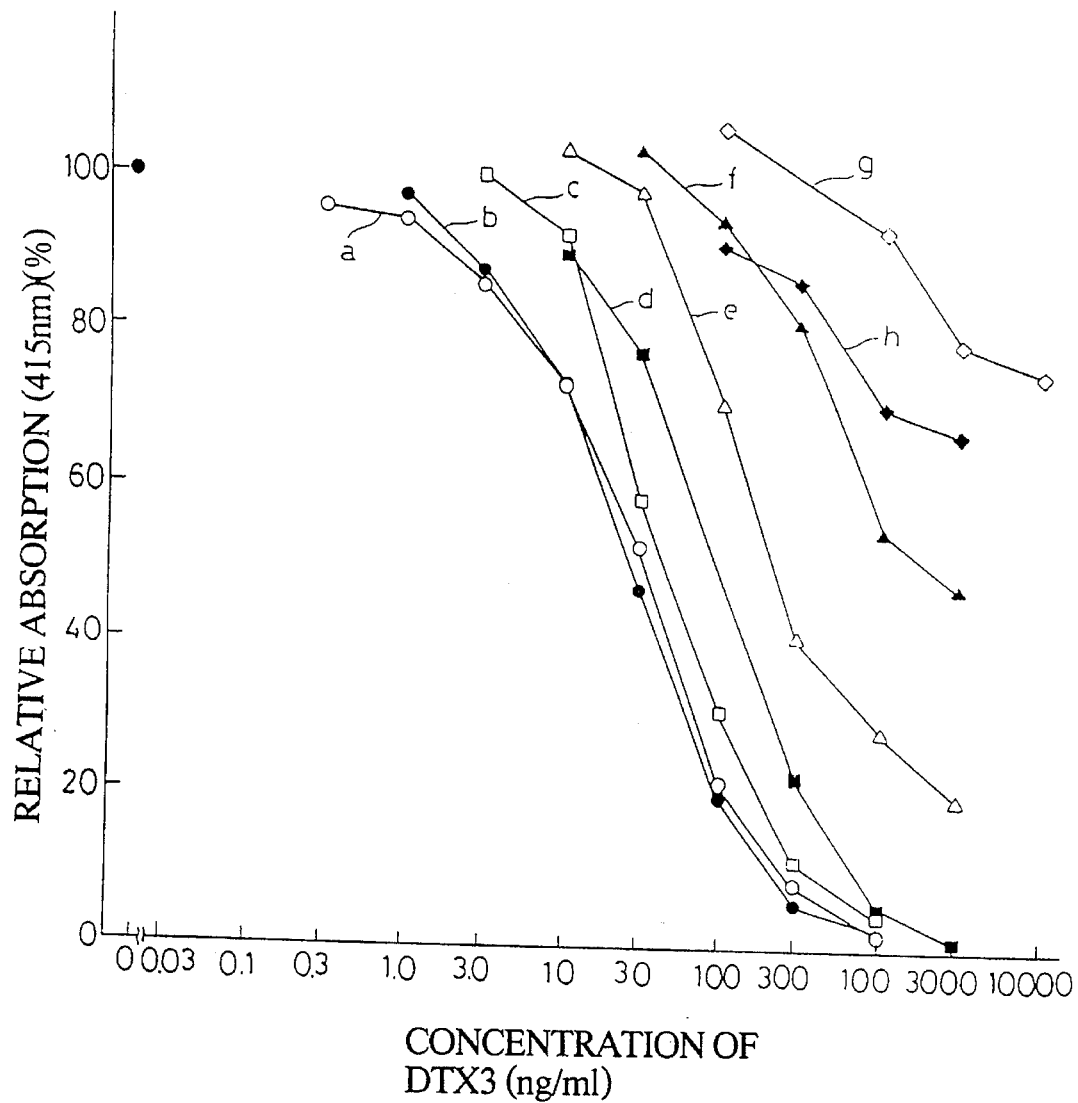
FIG. 14 is a graph showing the calibration curve in the case of measuring dinophysistoxin-3 by the competitive method.

The OA, DTX1 and DTX3 were measured by the competitive method in 8 steps of the methyl alcohol concentrations changing 10% increments from 0% to 70%, using the standard solution prepared by the method described in Example 6 and the ELISA plates carrying the OA-423 antibody prepared under the conditions of Example 3, and standard curves were produced therefrom. The results are shown in FIGS. 12 to 14. For all of the three kinds of shellfish poisons, a calibration curve can no longer be obtained, when the methyl alcohol concentration is over 50%. The reason is believed that the reactivity of OA, DTX1 and DTX3 with respect to the immobilized OA-423 antibody becomes relatively weaker than the reactivity of the OA-POD thereto and the competitive reaction does not occur. A measurement system having the methyl alcohol concentration of not more than 30% was able to obtain satisfactory results.

In the measurement of the OA by the competitive method, the range of the quantitative determination under the methyl alcohol concentration of 0 to 20% is 0.3 to 30 ng/ml. The range of the quantitative determination under 30% methyl alcohol is 1.0 to 100 ng/ml. Therefore, the quantitative determination can be effected at a higher sensitivity than that by the noncompetitive method (FIG. 12).

In the case of DTX1, the range of the quantitative determination under the methyl alcohol concentration of not more than 10% is 1.0 to 100 ng/ml. If the methyl alcohol concentration is raised to 30%, the range drops to 30 to 3000 ng/ml (FIG. 13).

In the case of DTX3, a low concentration of methyl alcohol considerably affects the sensitivity. The range of the quantitative determination of DTX3 under the methyl alcohol concentration of not more than 10% is 1.0 to 300 ng/ml. If the methyl alcohol concentration is raised to 30%, the range drops to 10 to 1000 ng/ml (FIG. 14).

The relationship between the reactivity of OA, DTX1, and DTX3 with respect to the OA-423 antibody and the methyl alcohol concentration is shown in the following Table 2. As clear therefrom, in the overall range of the methyl alcohol concentration of 0 to 40%, the ratios of the reactivity of OA423 antibody and DTX1 or DTX3, to that of OA423 antibody and OA were at least about 1/10 or higher in the case of the reactivity of OA being 1.

TABLE 2

| Methyl alcohol concentration (%) | OA | DTX1 | DTX3 |
| --- | --- | --- | --- |
| 0 | 1 | 0.5 | 0.09 |
| 10 | 1 | 0.33 | 0.10 |
| 20 | 1 | 0.08 | 0.08 |
| 30 | 1 | 0.10 | 0.10 |
| 40 | 1 | 0.16 | 0.23 |

INDUSTRIAL APPLICABILITY

Hitherto, when measuring a hydrophobic but lipophilic compound, the hydrophobic but lipophilic compound no be examined was extracted from the sample by an appropriate organic solvent, purified, and then subjected to various types of instrumental analyses. To the contrary, in the method for determining a lipophilic compound according to the present invention, the extract obtained by treating the sample with an organic solvent can be used as the sample for immunoassay directly without any further treatment or only after dilution with water, and further, an antigen-antibody reaction can be performed between the lipophilic compound included in the extract and the organic solvent-resistant antibody specific to the lipophilic compound. Therefore, the determination can be performed extremely conveniently and accurately with a high precision.

Further, the conventional method for determining lethal activity used for measuring diarrheal shellfish poisons had problems in the management of animals, the detection sensitivity, the precision, and the specificity. Even the conventional competitive enzyme immunoassay had the defect that the detection or measurement of DTX3 among the diarrheal shellfish poisons was impossible. To the contrary, the present invention provides a monoclonal antibody having specificity to all of the three types of diarrheal shellfish poisons; OA, DTX1 and DTX3, and so the defects of the conventional methods can be eliminated. Further, when the monoclonal antibody has resistance to organic solvents, it is possible to use the extract of the organic solvent from the sample in the detection or measurement step without any further treatment or only after dilution. Therefore, not only the detection or measurement step becomes more convenient, but also a high precision and a high sensitivity can be achieved. Therefore, contribution is possible to food sanitation or the like.

We claim:

1. A method for detecting the presence of okadaic acid, dinophysistoxin-1 and/or dinophysistoxin-3 in a sample, comprising:

providing a monoclonal antibody OA-423 produced by the hybridoma OA-423 strain (FERM BP-3943) which is specific to okadaic acid, dinophysistoxin-1 and dinophysistoxin-3, and which is tolerant to an organic solvent selected from the group consisting of aqueous methyl alcohol wherein a concentration of methyl alcohol is not less than 50%, methyl alcohol, ethyl alcohol/methyl alcohol, acetone/methyl alcohol, diethyl ether/methyl alcohol and benzene/methyl alcohol;

contacting a sample with said monoclonal antibody in the presence of said organic solvent under non-competitive reaction conditions;

determining whether an antigen-antibody reaction has occurred in the presence of said solvent.

2. A method for detecting the presence of okadaic acid, dinophysistoxin-1 and/or dinophysistoxin-3 in a sample, comprising:

providing a monoclonal antibody OA-423 produced by the hybridoma OA-423 strain (FERM BP-3943) which is specific to okadaic acid, dinophysistoxin-1 and dinophysistoxin-3, and which is tolerant to aqueous or absolute methyl alcohol;

measuring the differences, due to the concentration of said methyl alcohol, in reactivity of said monoclonal antibody with each of okadaic acid, dinophysistoxin-1 and dinophysistoxin-3, under non-competitive reaction conditions;

selecting at least two predetermined concentrations of methyl alcohol to differentially determine okadaic acid, dinophysistoxin-1 or dinophysistoxin-3;

contacting said sample with said monoclonal antibody in the presence of each of said aqueous or absolute methyl alcohols of said at least two predetermined concentrations, under non-competitive reaction conditions;

determining whether an antigen-antibody reaction has occurred in the presence of said aqueous or absolute methyl alcohols.

3. The method according to claim 2, wherein said two predetermined concentrations of methyl alcohol are 20% and 70%.

4. A method for detecting the presence of okadaic acid, dinophysistoxin-1 and/or dinophysistoxin-3 in a sample, comprising:

providing a monoclonal antibody OA-423 produced by the hybridoma OA-423 strain (FERM BP-3943) which is specific to okadaic acid, dinophysistoxin-1 and dinophysistoxin-3, and which is tolerant to 60% or less aqueous methyl alcohol;

measuring the differences, due to the concentration of said methyl alcohol, in reactivity of said monoclonal antibody with each of okadaic acid, dinophysistoxin-1 and dinophysistoxin-3, under non-competitive reaction conditions;

selecting at least two predetermined concentrations of methyl alcohol to differentially determine okadaic acid, dinophysistoxin-1 or dinophysistoxin-3;

contacting said sample with said monoclonal antibody in the presence of each of said aqueous methyl alcohols of said at least two predetermined concentrations, under competitive reaction conditions;

determining whether an antigen-antibody reaction has occurred in the presence of said aqueous or absolute methyl alcohols.

5. The method according to claim 4, wherein the concentration of said aqueous methyl alcohol is about 50% to differentially determine dinophysistoxin-3.

6. The method according to claim 4, wherein said concentration of said aqueous methyl alcohol is 40% or less.

* * * * *

UNITED STATES PATENT AND TRADEMARK OFFICE
CERTIFICATE OF CORRECTION

PATENT NO.   :  5,525,476
DATED        :  June 11, 1996
INVENTOR(S)  :  SHIRO MATSUURA, ET AL.

It is certified that error appears in the above-indentified patent and that said Letters Patent is hereby corrected as shown below:

Claim 4, col. 16, line 19, delete "non-competitive" and insert --competitive--.

Signed and Sealed this

Twenty-fourth Day of June, 1997

Attest:

BRUCE LEHMAN

*Attesting Officer*   *Commissioner of Patents and Trademarks*